United States Patent
Ferguson et al.

(10) Patent No.: US 7,611,860 B2
(45) Date of Patent: Nov. 3, 2009

(54) INDICATOR FOR IN-SITU DETECTING OF LYSOZYME

(75) Inventors: Drew M Ferguson, Cambridge (GB); Guy D. Milan, Great Shelford (GB); Crawford S. Dow, Coventry (GB); Uthaya Swoboda, Coventry (GB)

(73) Assignee: Cambridge Meditech Limited, Cambridge (GB)

( * ) Notice: Subject to any disclaimer, the term of this patent is extended or adjusted under 35 U.S.C. 154(b) by 877 days.

(21) Appl. No.: 10/381,426

(22) PCT Filed: Oct. 15, 2001

(86) PCT No.: PCT/GB01/04588

§ 371 (c)(1), (2), (4) Date: Jul. 15, 2003

(87) PCT Pub. No.: WO02/30478

PCT Pub. Date: Apr. 18, 2002

(65) Prior Publication Data

US 2004/0043422 A1   Mar. 4, 2004

(51) Int. Cl.
C08L 5/08 (2006.01)
G01N 33/53 (2006.01)
C12Q 1/34 (2006.01)

(52) U.S. Cl. .................. 435/18; 435/7.2; 106/162.1
(58) Field of Classification Search .......... None
See application file for complete search history.

(56) References Cited

U.S. PATENT DOCUMENTS

| | | | | |
|---|---|---|---|---|
| 3,990,895 A | * | 11/1976 | Land | 430/383 |
| 4,003,709 A | | 1/1977 | Eaton et al. | |
| 4,056,392 A | * | 11/1977 | Scott | 430/228 |
| 4,463,082 A | * | 7/1984 | Ferguson et al. | 430/228 |
| 4,622,297 A | * | 11/1986 | Kappner et al. | 435/32 |
| 5,181,905 A | * | 1/1993 | Flam | 602/41 |
| 5,735,812 A | * | 4/1998 | Hardy | 602/43 |
| 5,753,285 A | | 5/1998 | Horan | |
| 6,051,388 A | | 4/2000 | Bodenhamer | |
| 6,280,912 B1 | * | 8/2001 | Whitesides et al. | 430/350 |

FOREIGN PATENT DOCUMENTS

| | | |
|---|---|---|
| EP | 0 430 608 | 6/1991 |
| EP | 0 864 864 | 9/1998 |
| GB | 2 350 677 | 12/2000 |
| JP | 01272486 A * | 10/1989 |
| JP | H1-272486 | 10/1989 |
| JP | 02029380 A * | 1/1990 |
| JP | 04174578 A * | 6/1992 |
| JP | 04179578 A * | 6/1992 |
| WO | WO 89/05978 * | 6/1989 |
| WO | WO 97/46265 | 12/1997 |
| WO | WO 99/00151 | 1/1999 |
| WO | WO 99/12581 | 3/1999 |

OTHER PUBLICATIONS

Lloyd et al. Studies in Gas Production by Bacteria; The Biochemical Journal, vol. 24, No. 2 (1930) pp. 529-548.*
Peruski et al. Immunological Methods for Detection and Identification of Infectious Disease and Biological Warfare Agents; Clinical and Diagnostic Laboratory Immunology, vol. 10, No. 4 (2003) pp. 506-513.*
Bannikova et al. Hydrolysis of Chitosan Sulfate With an Enzyme Complex From Streptomyces Kurssanovii; Applied Biochemistry and Microbiology, vol. 38, No. 5 (2002) pp. 486-489.*
Nordtveit et al. Degradation of Partially N-Acetylated Chitosans With Hen Egg White and Human Lysozyme; Carbohydrate Polymers, vol. 29 (1996) pp. 163-167.*

* cited by examiner

Primary Examiner—Rebecca E. Prouty
Assistant Examiner—Paul C. Martin
(74) Attorney, Agent, or Firm—Nixon & Vanderhye P.C.

(57) ABSTRACT

The present invention provides an indicator for the in-situ detection of the presence of a lysozyme or a microbe producing lysozyme at a location. The indicator comprises a layer (8) which is susceptible to degradation by lysozyme and a signaling layer (7) which is adapted to produce a detectable signal which indicates the presence of the lysozyme or the microbe producing lysozyme which is located at substantially the same location as the lysozyme or microbe. In use, the signaling layer is at least initially protected from contact with the lysozyme or microbe which is located at substantially the same location as the lysozyme or microbe by the degradable layer.

28 Claims, 12 Drawing Sheets

INDICATOR FOR IN-SITU DETECTING OF LYSOZYME

This application is the US national phase of international application PCT/GB01/04588 filed 15 Oct. 2001 which designated the U.S.

FIELD OF THE INVENTION

The present invention provides a new indicator for the in situ detection of the presence of a substance or a microbe at a location, and methods for its use and construction.

BACKGROUND OF THE INVENTION

For a number of applications, it is important to be able to detect the presence of microbes at a given location, for example to determine whether foodstuffs are safe for consumption or whether a wound has become infected. There are currently a number of methods for the detection of the presence or absence of microbial contamination. However, these methods generally require a multistep assay to be performed in a laboratory or other clinical environment and not directly at the location where microbial contamination may exist.

During the process of wound healing there is often a serious danger of microbes entering a wound site, multiplying and resulting in the wound becoming infected. There are currently only indirect clinical methods of determining this condition. This is usually at a point at which infection has taken hold and is considered to be seriously detrimental to the patient. In extreme cases septicaemia will result. On the other hand it is well understood that over-frequent changing of a patient's dressing leads to sub-optimal wound healing.

A number of systems have been proposed which are intended to give nursing staff a prior warning of exudate striking through the surface or edges of a dressing and hence provide an indication of when a dressing should be replaced. These include the SignaDress (Trademark) dressing, available from Bristol-Myers Squibb, which has a transparent cover sheet on which a circular line is printed. When exudate from the wound is absorbed by the dressing, an area of moisture is evident through the cover sheet, and its spreading towards the line indicates that the dressing should be changed. EP-A-0541251 discloses a pad including a substrate that allows the extent of wound exudate absorption to be viewed therethrough. WO-A-99112581 discloses a wound dressing including an indicator layer which contains a dye that changes colour on contact with water.

Other systems have been proposed, intended to give nursing staff an indication of when a dressing should be replaced. For example, EP-A-0430608 discloses a wound dressing including a temperature-sensing liquid crystal tape; there is no evident means of distinguishing the possible causes of increased temperature, which may or may not be indicative of the need to change the dressing.

Current wound management is performed largely on an entirely subjective basis. None of the systems proposed above provide an indication of wound condition or of the presence of microbial contamination at a wound site.

In the personal care, clinical nutrition, pharmaceutical, dairy, beverage and food industries, rapid and traditional microbiological methods exist to monitor product quality during and immediately following the production process. However, this approach has the disadvantage that these tests are performed on a small random selection of the total production batch, and are therefore helpful only in indicating gross contamination problems at the point of manufacture. No information on microbial activity is given to the end user up to the point at which the product is deemed to have reached the end of its shelf-life. Furthermore, once the packaging has been breached, for example by the action of opening and subsequent reuse of the product, opportunistic organisms can contaminate the product. The presence of these micro-organisms can jeopardise the quality and organoleptic characteristics of the product, compromise performance, and shorten shelf-life. Also traditional methods of microbiological detection tend to be selective and may miss certain species of organism.

Micro-organisms of particular concern include the opportunistic Pseudomonads which are environmental organisms found in soil and water. These bacteria have minimal nutritional needs and can metabolize and grow almost anywhere. Other hazardous organisms of concern to consumers include *E. coli* in beef, *listeria* on soft cheeses and *salmonella* in poultry.

Particularly vulnerable forms of foodstuffs include UHT (ultra heat treated)/ESL (extended shelf-life) dairy products, cook-chill products and raw meats.

Consumers are becoming more demanding and expecting products to contain more natural ingredients with fewer preservatives, together with the added requirements of having longer shelf-life and the ability to perform under difficult conditions. These customer trends are powerful and can increase the risk of contamination both at the point of manufacture and whilst the product is in use in the hands of the customer. The need therefore for a method of providing a continuing check on the level of bioburden in these products is clear.

DESCRIPTION OF THE INVENTION

According to the invention there is provided an indicator suitable for detecting the presence of a substance or a microbe at a location which indicator comprises:
 (a) a layer which is susceptible to degradation by the substance or microbe or a first substance associated with the microbe; and
 (b) a signalling layer which is adapted to produce a detectable signal which signalling substance indicates the presence of the substance or microbe or a second substance associated with the microbe or a further substance which is at substantially the same location as the substance or microbe;

wherein, in use, the signalling layer (b) is at least initially protected from contact with the substance or microbe or the second substance associated with the microbe or the further substance which is at substantially the same location as the substance or microbe by the layer (a).

The signalling layer may be adapted to produce a detectable signal whose initial strength is proportional to the amount of the substance, microbe or of the second substance associated with the microbe, which is present. Thus when there is a comparatively large amount of the substance, microbe or of the second substance associated with the microbe present, the detectable signal is initially strong or when there is a comparatively small amount of the substance, microbe or of the second substance associated with the microbe present, the detectable signal is initially weak.

It will be understood that it is the initial strength of the signal which is important because for some substances or microbes, the activity of the substance or microbe is not quenched on contact with the signalling layer. Thus, after a period of time, even when the amount of the substance or microbe is comparatively small, it will act on the signalling layer until all of the layer is producing the detectable signal with the result that the final detectable signal is strong.

One advantage of the invention is that it can give an indication of when the amount of a substance or microbe at a particular location has reached a predetermined amount, for example a dangerous level or, in the case of a microbe where the location is a wound in a human or animal, a level at which infection might develop. For example, where the location is a foodstuff, the amount of the microbe to be detected could be an amount at which the foodstuff is dangerous to eat.

A further advantage of the invention is that it can measure the body's response to the presence of microbes rather than the microbes themselves. The invention therefore provides a more relevant indication of a clinical problem.

A further advantage of the invention is that whilst traditional methods of microbiological detection tend to be selective and may miss certain species of microbe, the current invention has the advantage over these traditional methods in that it gives a measure of general not specific microbial contamination.

Another advantage of the invention is that a background level of a first substance which may be present at a location will enable a positive signal in the indicator regardless of whether a contaminating substance or a microbe is present. The time required for this reaction to occur is significantly longer than the time required for a reaction to occur when a contaminating substance or microbe is present and therefore can provide the user with an indication of when the product has reached the end of its working life.

The sensitivity of the indicator according to the invention is determined by the nature of layer (a). It can be seen that the thicker layer (a) is, the higher the amount of the substance, microbe or the first substance associated with the microbe, or the longer the period of time that the layer (a) is exposed to the substance or microbe or the first substance associated with the microbe, has to be before the layer (a) is degraded sufficiently to allow the substance or microbe or the second substance associated with the microbe or the further substance which is at substantially the same location as the substance or microbe to contact the indicator.

The thickness of layer (a) and the material used to make it is preferably chosen according to the location at which the indicator is to be used such that when the indicator is designed to detect the presence of a microbe or of substance(s) associated with a microbe, the layer (a) is structured such that the signalling layer produces a detectable signal before the concentration of the microbe reaches a dangerous level. On the other hand, the layer (a) should be sufficiently robust that the time required before it is degraded by a background level of a microbe or of a first substance associated with a microbe is long enough such that the indicator has a useful working life. The thickness of layer (a) and the material used to make it can easily be determined by trial and error by a person of skill in the art when the location at which the indicator is to be used and the type of microbe which is likely to be present are known.

The indicator according to the invention can optionally take a range of physical forms depending on the location at which it will be placed. For example, it could be in the form of a disc which comprises the two layers (a) and (b) in substantially planar form or the layer (b) could be in substantially planar form and layer (a) could at least partially (for example by being in the form of a cup such that one face and the sides of layer (b) are covered by layer (a)) or wholly encapsulate layer (b). Alternatively the indicator according to the invention could be in tubular form wherein the core of the tube comprises layer (b) which core is coated by layer (a). An example of a suitable tubular form of the indicator according to the invention is a coated thread.

The location at which the amount of a substance or microbe is to be detected may be a human or animal location, particularly a living human or animal body, for example, a wound; a domestic location, e.g. a kitchen or bathroom; a laboratory location; an industrial location, e.g. a steriliser or machinery or a surface involved in the production of pharmaceutical products or food products; or a foodstuff or a personal care product.

The layer (a) is preferably adapted to be, in use, positioned proximate to the location. It may, for example, be such that it separates the location from the signalling layer. The layer (a) is preferably a biopolymer layer. Examples of suitable biopolymers for use in layer (a) include chitin, chitosan, keratan sulphate, hyaluronic acid, chondroitin, polyhydroxybutyrate, polyester amides, polytrimethylene succinate, albumin crosslinked polyvinylpyrrolidone and dextran.

The first and second substance associated with the microbe are optionally the same or different; preferably they are different. For example the layer (a) may be susceptible to degradation by a substance produced by the location in response to a microbe and the signalling layer may be adapted to indicate the presence of a substance produced by the microbe. Alternatively the layer (a) may be susceptible to degradation by a microbe and the signalling layer may be adapted to indicate the presence of a substance associated with the microbe or the layer (a) may be susceptible to degradation by a substance associated with a microbe and the signalling means may be adapted to indicate the presence of a microbe.

The first or second substance associated with the microbe is a substance generally produced at a location where there is a microbe. It may be, for example, a microbial by-product, a part of microbial cell contents, or a substance associated with the location's response to a microbe where the location is a living human or animal body.

A suitable example of a microbial by-product for use as the first or second substance associated with the microbe is an enzyme, particularly, an oxidase, lipase, tryptophanase, beta-lactamase or esterase, dehydrogenase, kinase, hydrolase, protease, nuclease, phosphatase, decarboxylase, and/or carboxylase. The microbial by-product may also be a naturally occurring organic phosphate such as adenosine triphosphate (ATP), a pyridine nucleotide such as nicotinamide adenine dinucleotide (NADH) or a flavin such as flavin adenine dinucleotide (FADH). A suitable example of a substance associated with the location's response to a microbe where the location is a living human or animal body is an immune cell, an immune cell by-product, or an enzyme such as lysozyme, pepsin or dextranase. A suitable example of an immune cell for use as the second substance associated with the microbe is a neutrophil, basophil or eosinophil. In particular, when layer (a) comprises chitosan, the first substance associated with the microbe may be lysozyme, when it comprises polyester amide the first substance associated with the microbe may be a protease, when it comprises polytrimethylene succinate the first substance associated with the microbe may be a lipase, when it comprises albumin crosslinked polyvinylpyrrolidone the first substance associated with the microbe may be pepsin and when it comprises dextran the first substance associated with the microbe may be dextranase.

The signalling layer may be adapted to indicate the presence of a further substance found at substantially the same location as the substance or microbe. A signal will therefore be produced when the substance or microbe or first substance associated with the microbe has sufficiently degraded layer (a) so as to allow the further substance to contact the indicator. Accordingly, the signal indicates the presence of the substance or microbe. A suitable example of the further substance found at substantially the same location as the substance or microbe is a substance generally found in the environment such as water.

Alternatively a microbe itself may act directly on both the layer (a) and the signalling layer thereby producing the detectable signal. The microbe is, for example, a micro-organism, e.g. bacteria, yeast or fungi.

The signalling layer preferably indicates the presence of a metabolic by-product from a microbe or, more particularly a bacterial cell. Generally as time progresses, the number of microbes multiplies, and the concentration of a metabolic by-product increases. The signalling layer preferably indicates the presence of an enzyme, more particularly an enzyme which is an esterase, oxidase, dehydrogenase, kinase, hydrolase, protease, nuclease, phosphatase, decarboxylase, and/or carboxylase.

The detectable signal is optionally detectable visually, audibly or electrically; preferably it is a visually detectable signal, e.g. a change in colour. For example the signalling layer comprises a dye, stain, indicator substance and/or a chromogenic or fluorogenic substrate. In one embodiment, the signalling layer comprises a moisture sensitive indicator such as silica or cobalt chloride. Preferably the dye, stain or substrate is initially a first colour but on contact with a substance, microbe, a substance associated with a microbe or a further substance which is located at substantially the same location as the substance or microbe, changes colour.

Examples of a suitable dye, stain, indicator substance or substrate include methylene blue, meldola's blue, phenol red, bromo-chloro-indolyl phosphate, alanine amidoacridone, fluorescein diacetate and/or a tetrazolium salt.

Where the location is a wound, it is possible for the signalling layer to measure an increase in immune cells such as neutrophils, basophils or eosinophils, as a response to infection. This may be achieved by the signalling layer indicating their presence directly or the presence of their accompanying chemical by-products. Accordingly the signalling layer may comprise an antibody assay or a bioassay as appropriate.

Alternatively the signalling layer may comprise a reagent that changes colour in the presence of a certain microbe. Current staining techniques in the laboratory enable the observation of microbes (particularly bacteria) directly. It is also possible to probe for bacteria using antigen specific antibodies, conjugated with an appropriate label for indirectly visualising the bacterial cells, in the signalling layer.

Alternatively the signalling layer comprises a pH indicator which detects whether the pH at the location is within a certain range. It is generally known that the presence of bacteria reduces the pH of the medium in which they are present. For example, the pH of wound exudate will change as the concentration of microbes in the wound increases.

The signalling layer is preferably formed from a membrane material, for example, PVDF, nitrocellulose, polysulphone, cellulose acetate, nylon, or a polymer with a hydrophilic component.

The indicator is optionally either adapted such that, in use, the layer (a) is positioned adjacent to the location or the layer (a) is separated from the location by one or more additional layers. Examples of suitable additional layers include an absorbent layer, a non-adhesive layer or an adhesive layer, and/or a removable protective layer which protects the layer (a) from damage before use (for example, it may take the form of a removable foil layer).

Optionally the indicator is provided with a protective layer which covers the signalling layer and protects it from degradation by an external substance, microbe or substance associated with a microbe. Preferably the protective layer is substantially transparent to the detectable signal produced by the signalling layer. Where the detectable signal is an electrically detectable signal, the protective layer preferably comprises electrically conductive portions in order to connect to the signalling layer. Optionally the protective layer is sufficiently stiff to support the indicator and to give it structural rigidity.

Optionally the indicator is provided with a collar to give it support and/or structural rigidity. The collar may optionally be provided with a spike or adhesive means in order to fix the indicator at the location.

The indicator is preferably for use in an environment wherein the signalling layer of the indicator is protected from contact with the environment at least initially. The environment is preferably a liquid, more preferably an aqueous environment; for example a tissue culture medium or foodstuff.

The indicator according to the invention may usefully be included in a dressing for a wound or a suture. According to the invention there is further provided a dressing for a wound, which comprises a dressing layer and an indicator according to the invention. For the purposes of this specification, the term "dressing" includes bandages, i.e. in which the wound-contacting part of the system is part of a larger product.

One advantage of including an indicator according to the invention in a dressing for a wound is that it may indicate when the dressing needs to be changed. This is because the indicator will indicate when infection in the wound has reached a predetermined level. Generally this level is chosen such that there is substantially no risk of the patient becoming diseased. On the other hand the level is sufficiently high that the dressing is not replaced too often.

The dressing layer may optionally take any form generally known in the art. A full description of dressings and wound management, including the various types of dressing layer that may be used in this invention, may be found in "A Prescriber's Guide to Dressings and Wound Management Materials" (March 1996) National Health Service, Wales; the content of this document is incorporated herein by reference.

For example the dressing layer could be a gauze pad having one or more plys, a non-adhesive gel type dressing such as a hydrogel, an adhesive gel-type dressing, a fluid interactive hydrocolloid dressing capable of adhering to both dry and moist skin surfaces or a hydrocolloid dressing including a polymeric foam layer.

The dressing according to the invention may optionally include further layers such as an adhesive layer and/or a removable protective layer.

The dressing according to the invention may also be provided with a moisture sensitive indicator adapted to indicate when the dressing is saturated with moisture. A suitable moisture sensitive indicator is, for example, cobalt chloride which changes from blue to pink in the presence of moisture.

The indicator is preferably included within the dressing according to the invention by moulding, welding or bonding to the dressing layer. Where the indicator is in the form of a tube or thread, it could optionally be included in the dressing according to the invention by being embroidered into the dressing layer.

Optionally the indicator forms an integral part of the dressing such that the signalling layer is impregnated into an area of a fabric layer of the dressing to which the degradable layer is attached in such a manner that its edges and the edges of the signalling layer are sealed. One suitable way of carrying this out is to coat a fibre of a fabric layer first with the signalling layer (b) and then with the degradable layer (a).

The dressing according to the invention may optionally further comprise, e.g. in the dressing layer, a conventional component such as an antiseptic agent, an anti-bacterial agent, and/or an emollient.

According to the invention there is further provided a suture which comprises an indicator according to the invention. The indicator may be attached to a thread or wire. In particular, the indicator may be included in the suture by moulding, welding or bonding, or, where the indicator is in the form of a tube or thread, it may be embroidered into the suture.

According to the invention there is further provided packaging for a foodstuff or a personal care product which packaging comprises a container layer and an indicator according to the invention.

Preferably, in use, the layer (a) of the indicator is in contact with the foodstuff or personal care product. Preferably the packaging according to the invention is adapted such that, in use, some or all of the signalling layer is visible.

The container layer used in the packaging according to the invention may comprise material generally known in the art. For example it may comprise one or more layers of a polymeric, plastics or paper material, e.g. a laminated polymeric, plastics or paper material. The indicator is preferably included within the container layer, e.g. by moulding, welding or bonding. Alternatively, the indicator may form a separate unit which is attached to or inserted directly in to the product.

One advantage of the packaging according to the invention is that it may give a visual indication of when a foodstuff is unfit or even unsafe to consume because the level of microbial contamination of the foodstuff has become unacceptably high. This is clearly safer than relying upon standard "use-by" dates which are generally printed on the packaging of foodstuffs, beverages and personal care products.

A further advantage of the indicator according to the invention is that it will monitor microbial activity throughout the entire usable life of the product, giving a continuing indication of whether the bioburden within the product has reached an unacceptable level and is therefore a measure of the product's continuing efficacy or suitability for use or consumption.

Aspects of the invention are illustrated by reference to the following drawings which are not intended to limit the scope of the invention disclosed:

Figure 1:
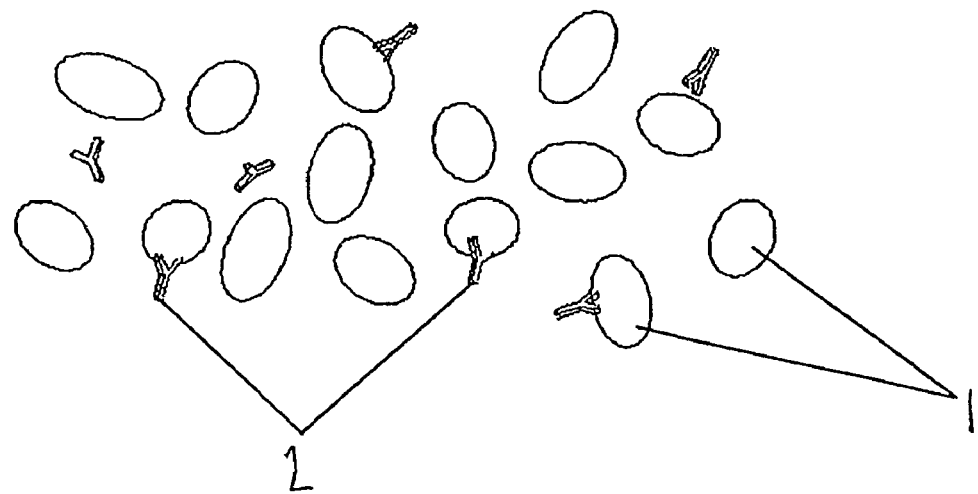
FIG. 1 is a schematic perspective view of lysozyme and microbes.
Figure 2:
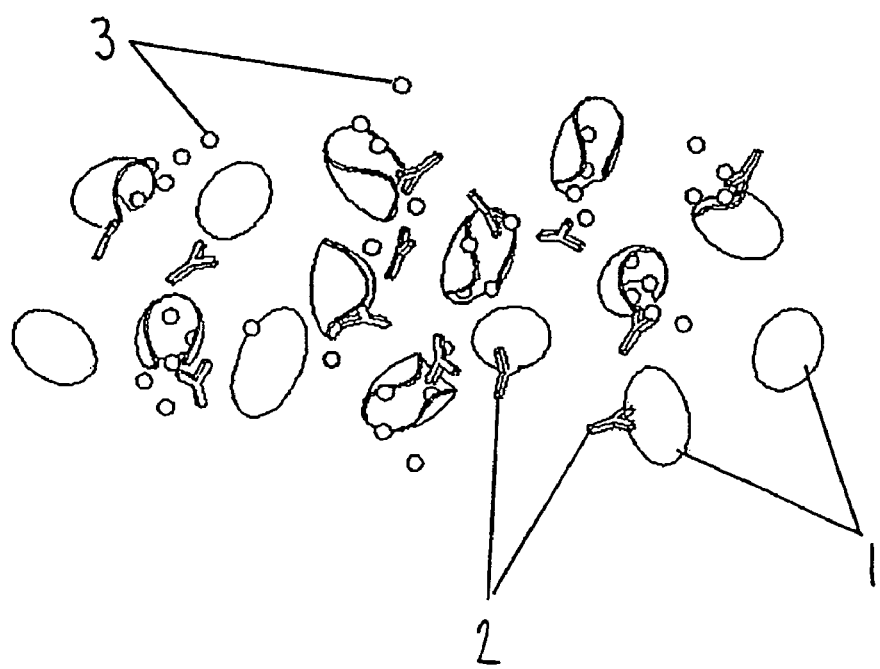
FIG. 2 is a schematic perspective view of microbes under attack from lysozyme and releasing NADH (nicotinamide adenine dinucleotide—reduced form)
Figure 3:
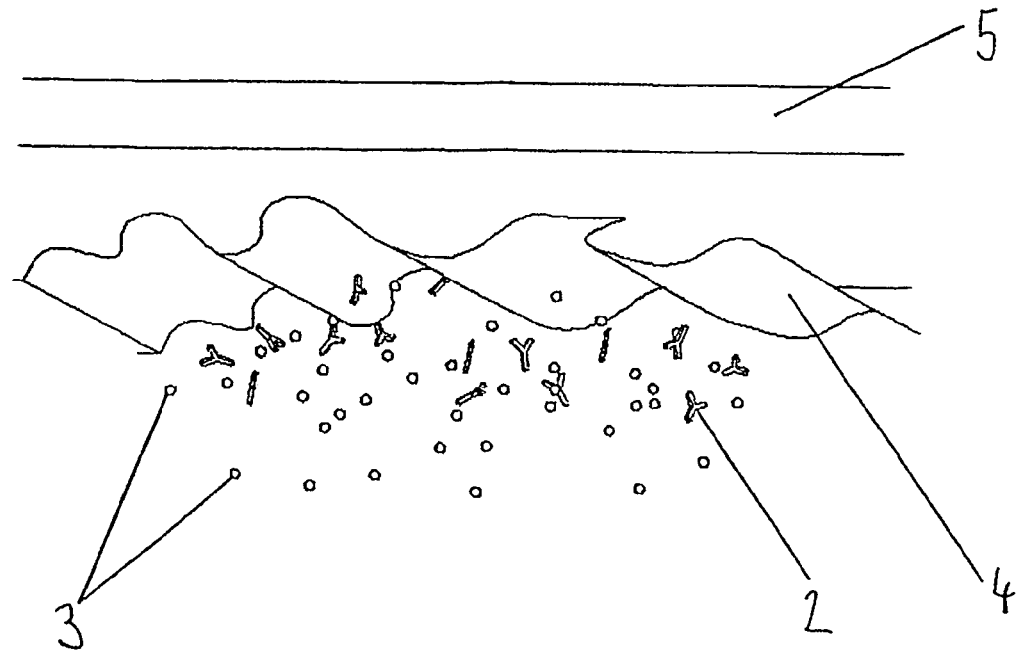
FIG. 3 is a schematic perspective view of lysozyme degrading a chitosan layer.
Figure 4:
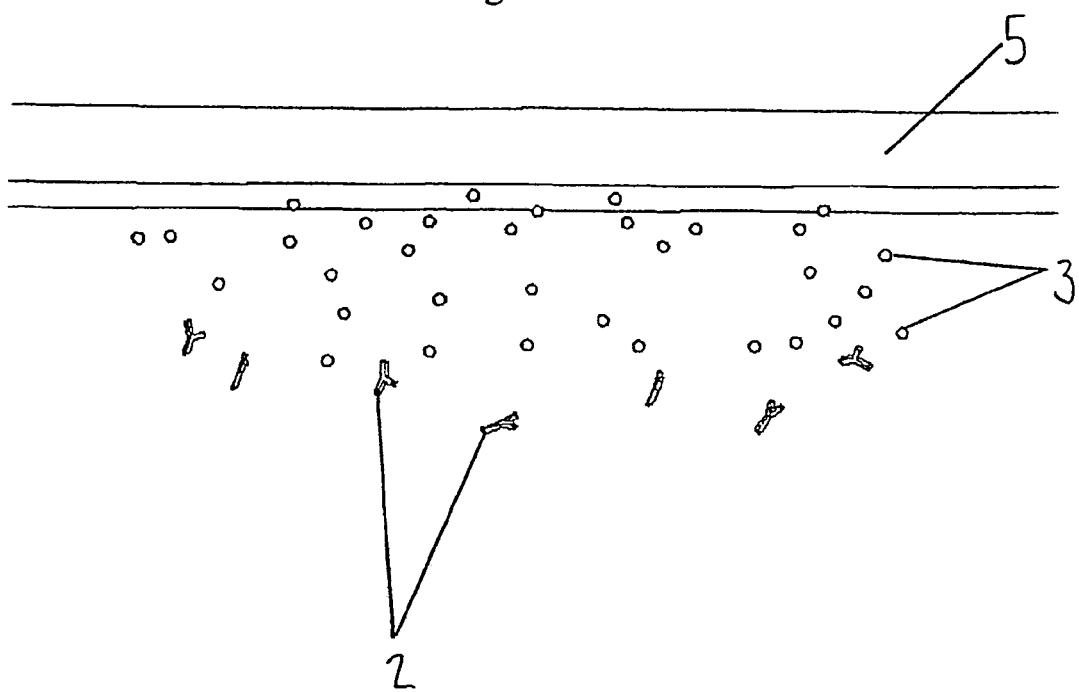
FIG. 4 is a schematic perspective view of NADH reacting with an indicator layer.
Figure 5:
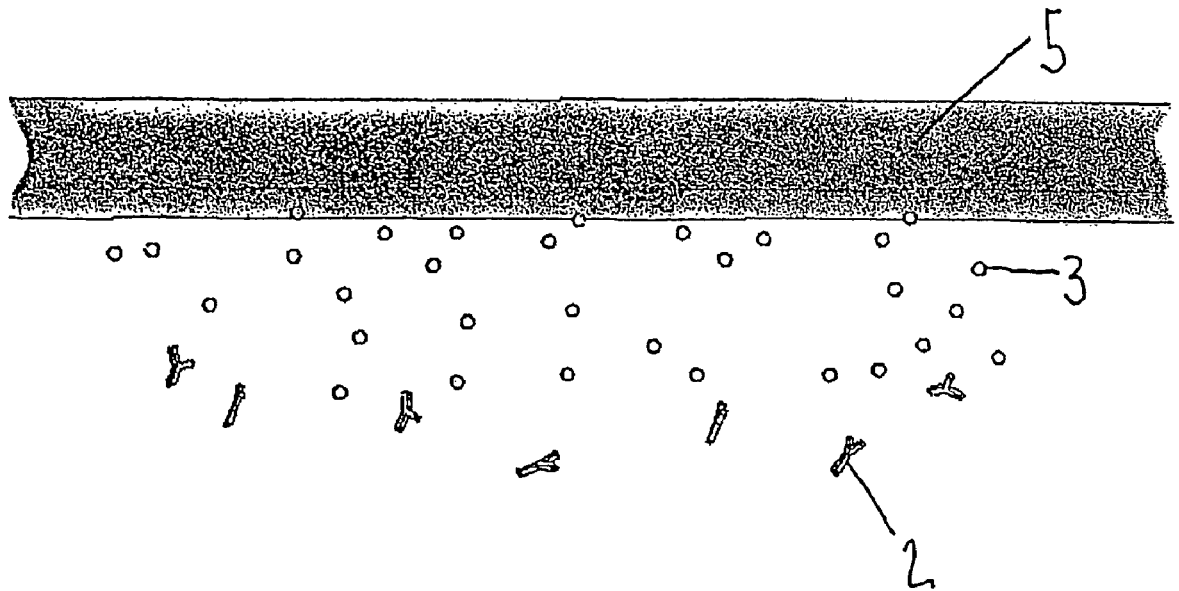
FIG. 5 is a schematic perspective view of NADH causing an indicator layer to change colour.

FIGS. 1 to 5 show schematically the biochemical principles which underpin one aspect of the invention where the location is a wound in a living human or animal body and the first substance associated with the microbe is lysozyme and the second substance associated with the microbe is NADH. In these Figures, microbes 1 are shown being attacked by lysozyme 2 such that NADH 3 is released; the lysozyme 2 degrades the chitosan layer 4 such that NADH 3 can react with the indicator layer 5 which then changes colour as shown in FIG. 5.

Figure 6:
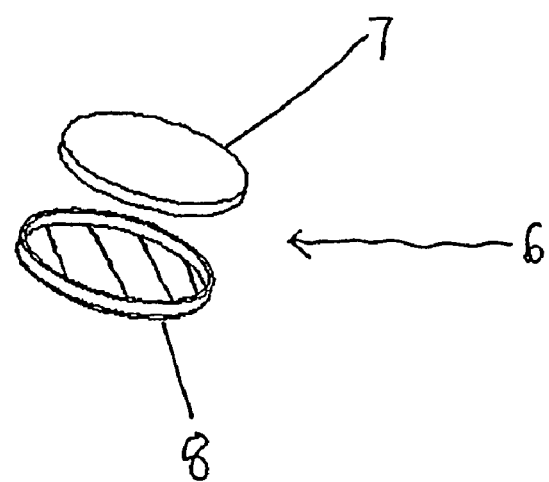
FIG. 6 is an exploded schematic perspective view of an indicator according to the invention.

FIG. 6 shows a first embodiment of an indicator according to the invention. The indicator 6 comprises a signalling layer in the form of disc 7 and a cup-shaped biopolymer layer 8. The biopolymer layer 8 is cup-shaped in order that one face and the edge of the indicator disc 7 is covered by the layer.

Figure 7:
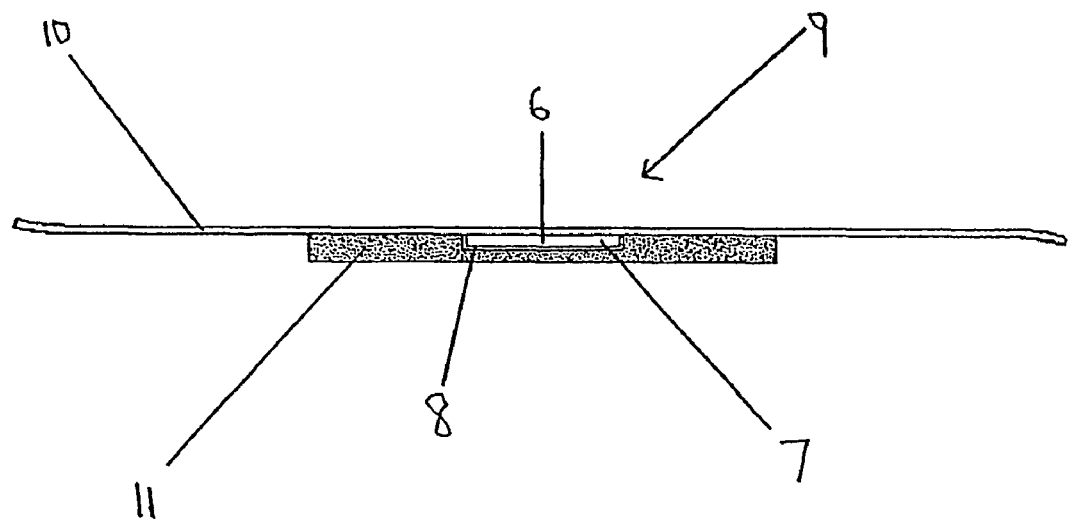
FIG. 7 is a schematic cross-sectional view of an island type dressing incorporating the indicator according to the invention which is shown in FIG. 6.
Figure 8:
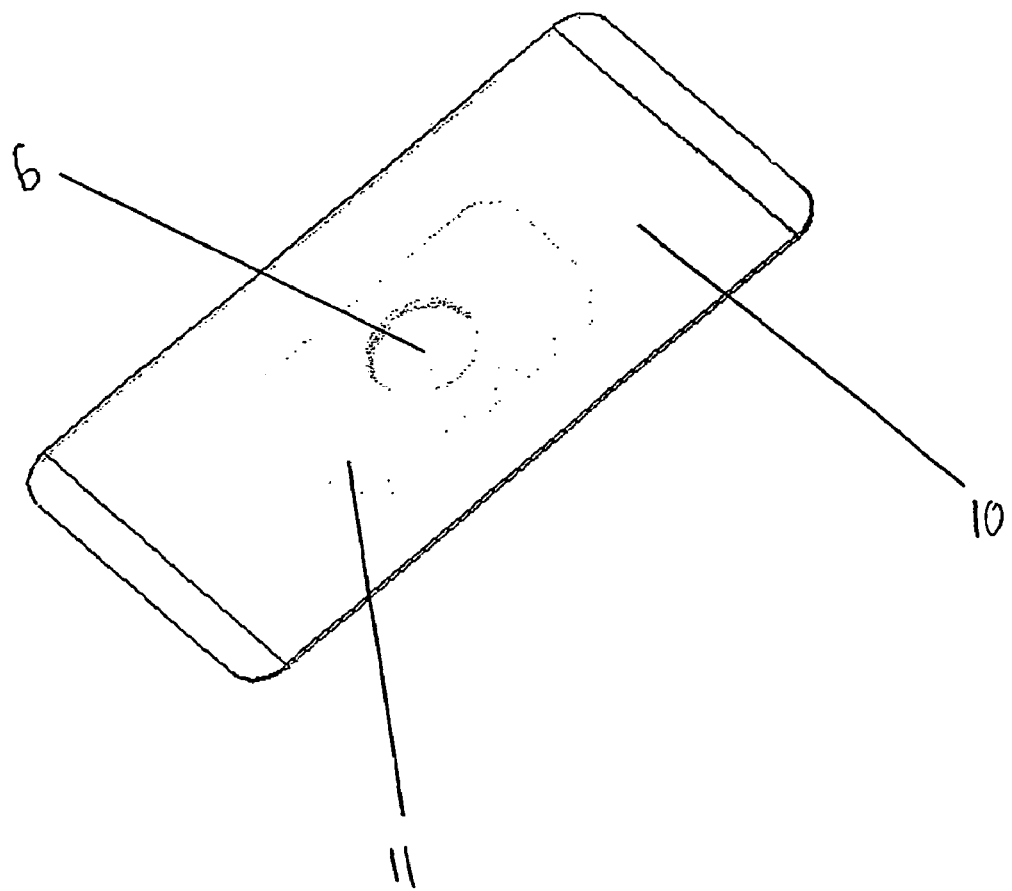
FIG. 8 is a schematic perspective view of the island type dressing shown in FIG. 7.
Figure 9:
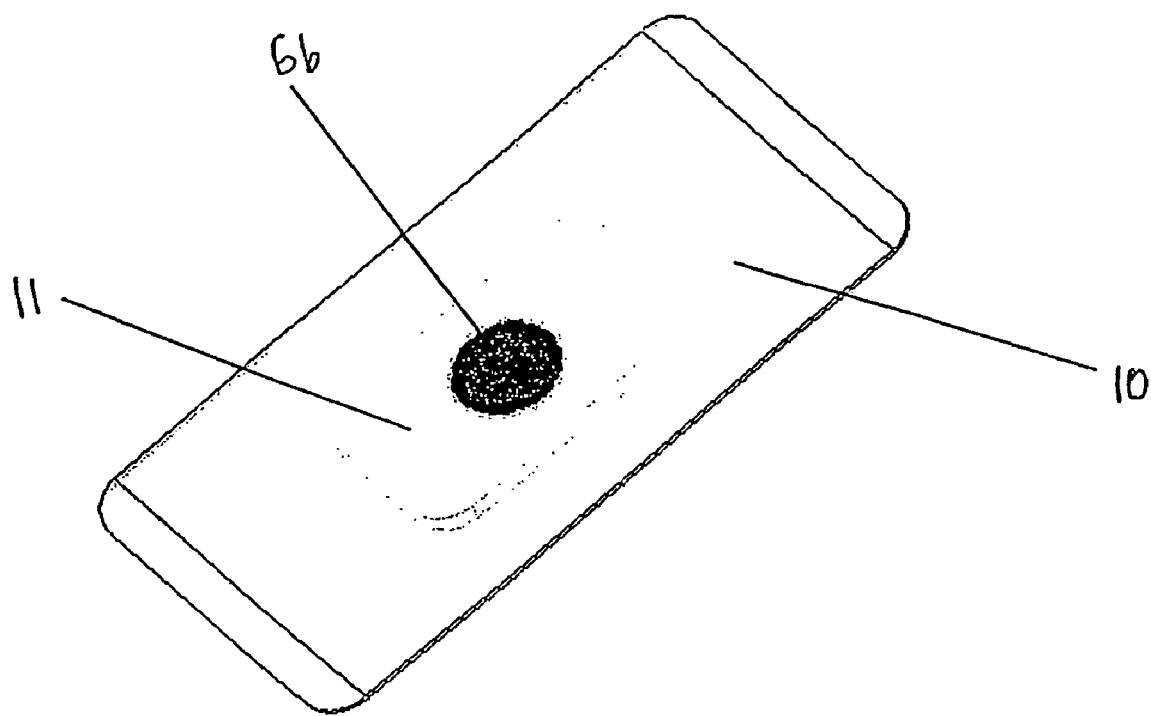
FIG. 9 is a schematic perspective view of the island type dressing shown in FIG. 7 where the signalling layer of the indicator is producing a detectable visual signal.

FIGS. 7 to 9 show the application of the indicator 6 according to the invention to an island type wound dressing 9 which comprises a transparent top sheet 10, a dressing pad 11 and an indicator 6 (or 6b when activated and the signalling layer is producing a detectable signal) which comprises a signalling layer 7 and a biopolymer layer 8. The signalling layer 7 of the indicator 6,6b is visible through the transparent top sheet 10 of the dressing 9.

Figure 10:
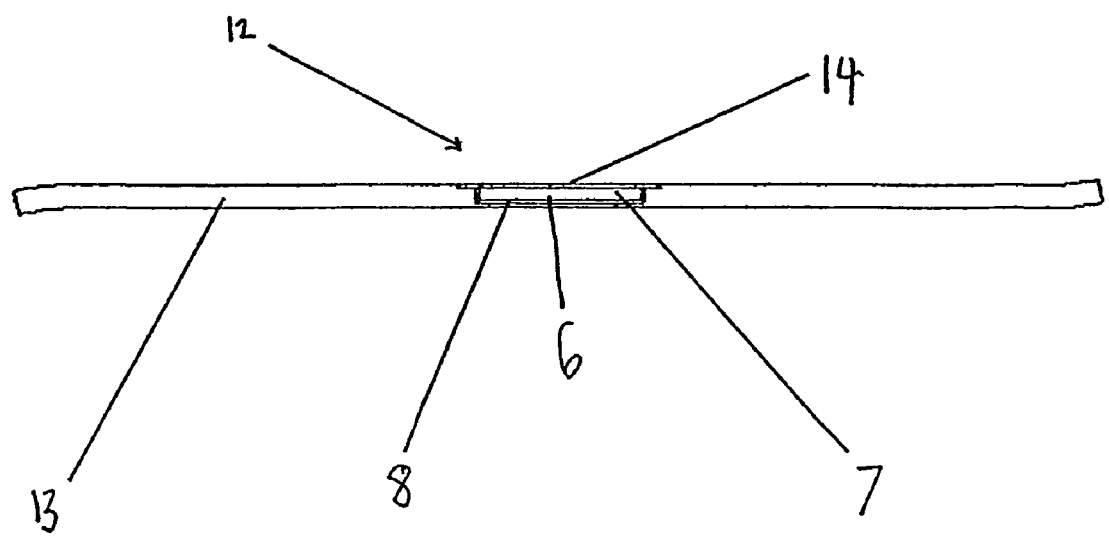
FIG. 10 is a cross-sectional view of a polyurethane type dressing comprising the indicator according to the invention which is shown in FIG. 6.
Figure 11:
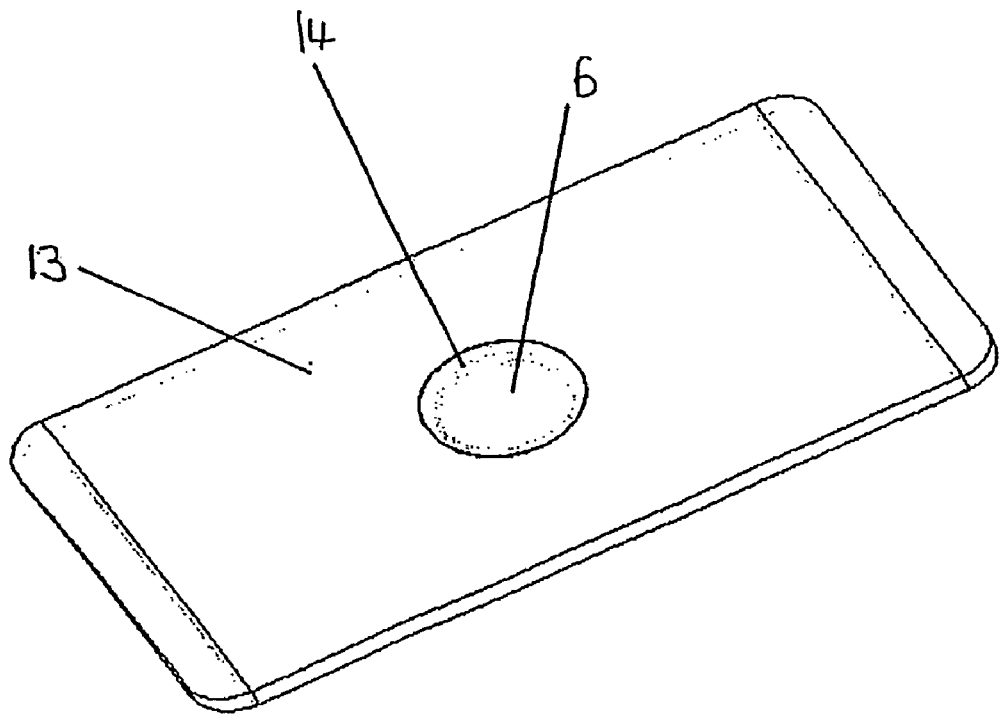
FIG. 11 is a perspective view of the polyurethane type dressing shown in FIG. 10.

FIGS. 10 and 11 show a polyurethane type dressing 12 which comprises a dressing sheet 13 having a window 14 underneath which is placed the indicator 6 which comprises signalling layer 7 and biopolymer layer 8.

Figure 12:
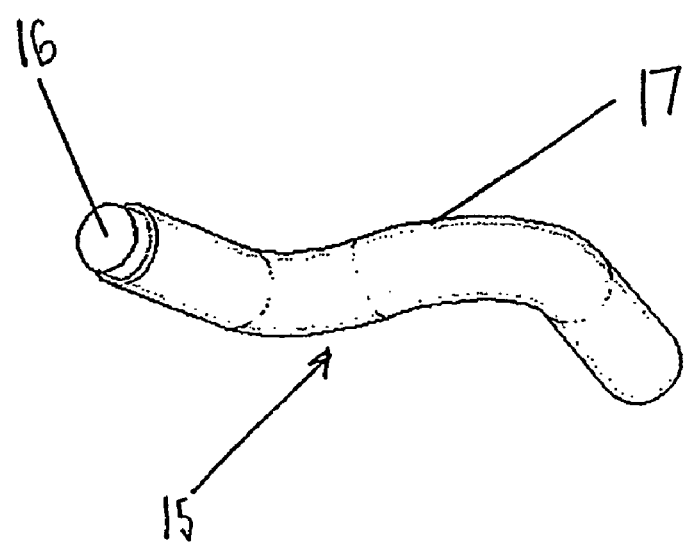
FIG. 12 is a perspective view of a further indicator according to the invention which is in the form of a coated thread.

FIG. 12 shows a second embodiment of the indicator according to the invention. The indicator 15 comprises a signalling layer which is in the form of a thread 16 which is coated by biopolymer layer 17.

Figure 13:
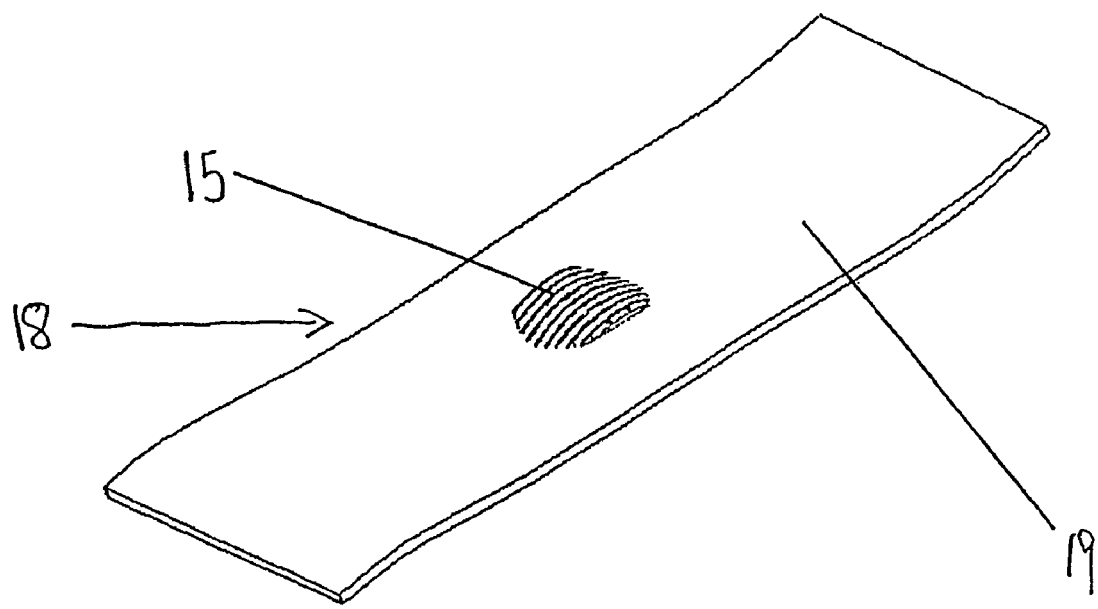
FIG. 13 is a perspective view of a fabric dressing incorporating the indicator according to the invention shown in FIG. 12 wherein the signalling layer of the indicator is producing a detectable visual signal.

FIG. 13 shows a fabric dressing 18 comprising the indicator 15 which is embroidered into the dressing layer 19.

Figure 14:
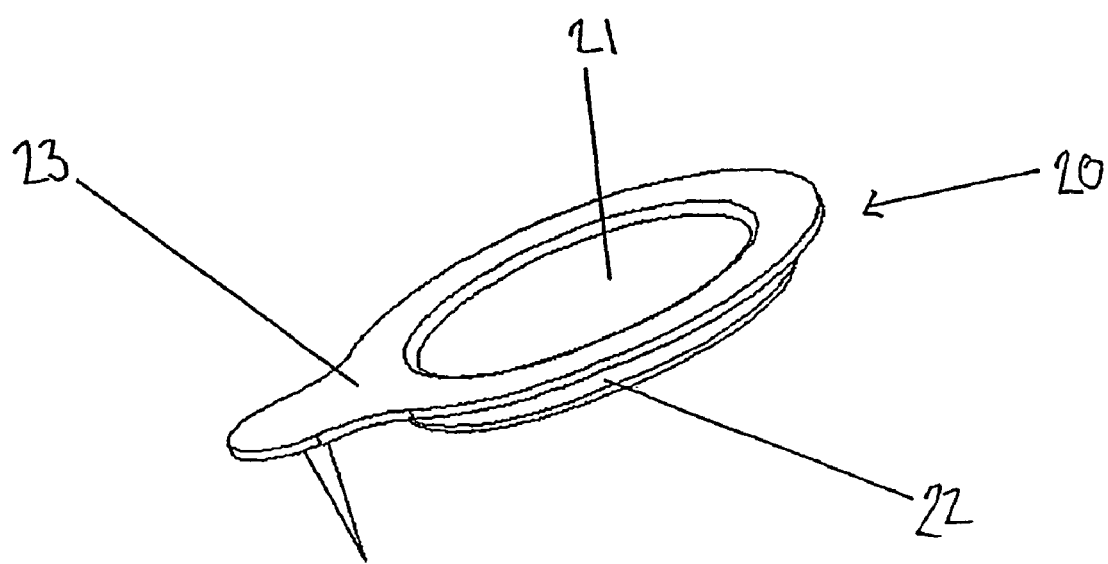
FIG. 14 is a perspective view of a further indicator according to the invention.

FIG. 14 shows a third embodiment of the indicator according to the invention. The indicator 20 comprises a signalling layer 21, a biopolymer layer 22 and a supporting collar 23.

Figure 15:
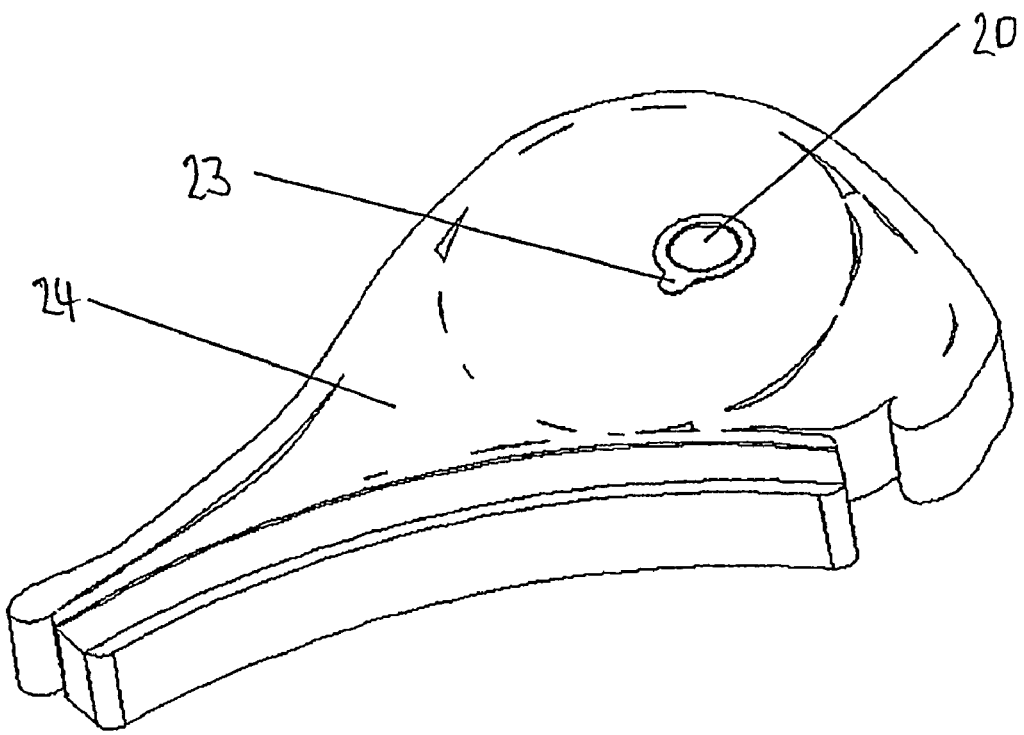
FIG. 15 is a perspective view of the indicator which is shown in FIG. 14 attached to a food product.
Figure 16:
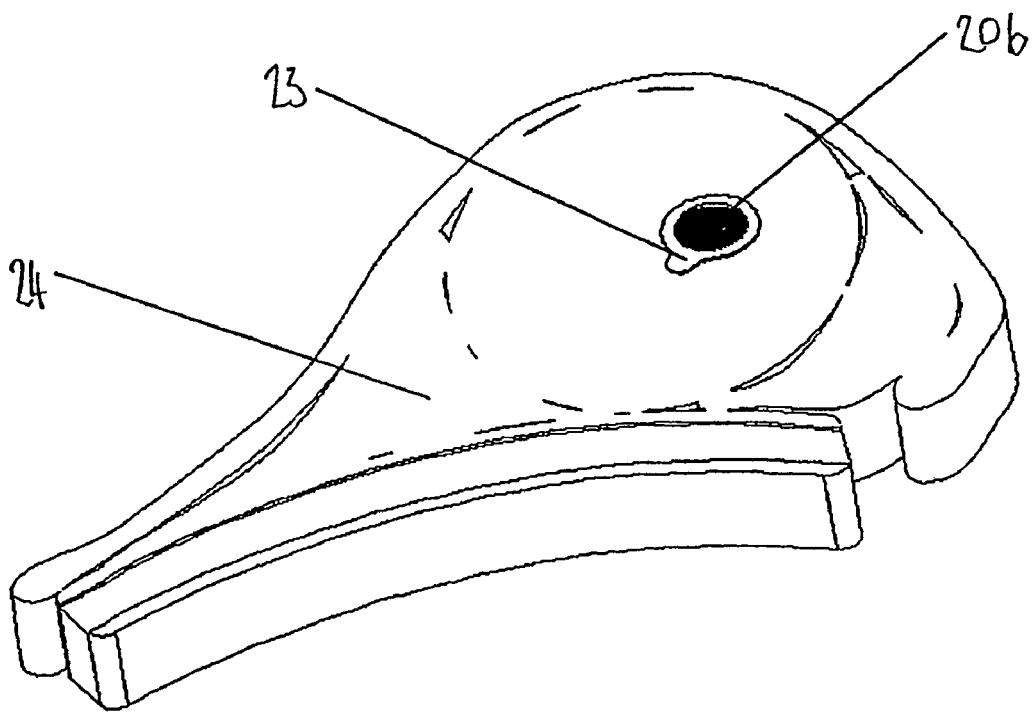
FIG. 16 is a perspective view of the indicator and food product which are shown in FIG. 15 wherein the signalling layer of the indicator is producing a detectable visual signal.

FIGS. 15 and 16 show a food product 24 to which the indicator 20,20b is attached by means of supporting collar 23. In FIG. 16, the signalling layer of indicator 20b is producing a detectable visual signal.

Figure 17:
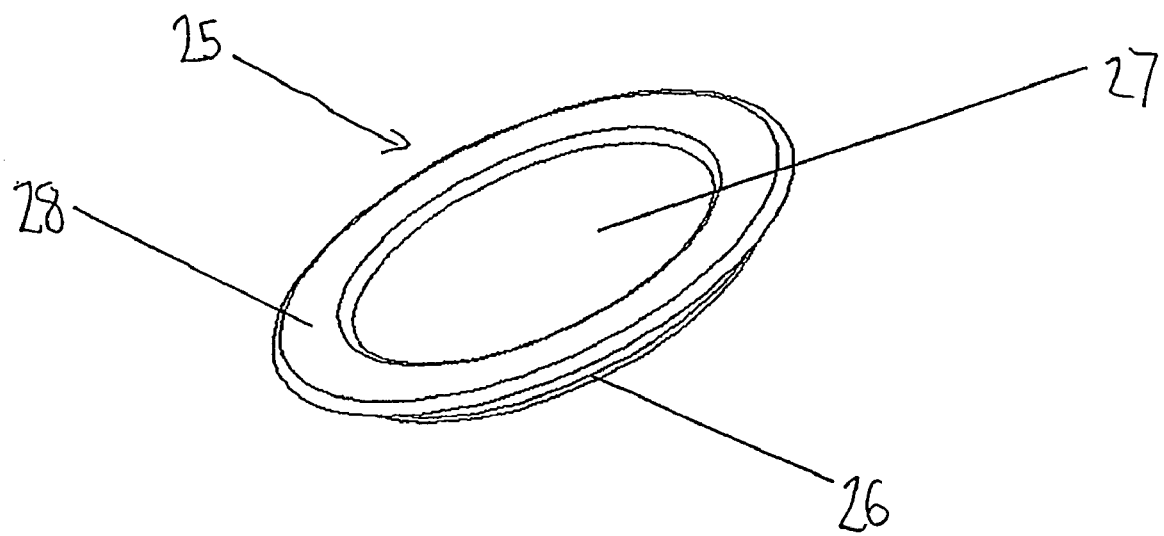
FIG. 17 is a perspective view of a further indicator according to the invention suitable for use with packaging for a liquid.

FIG. 17 shows a fourth embodiment of the indicator according to the invention. The indicator 25 comprises a biopolymer layer 26, signalling layer 27 and supporting collar 28.

Figure 18:
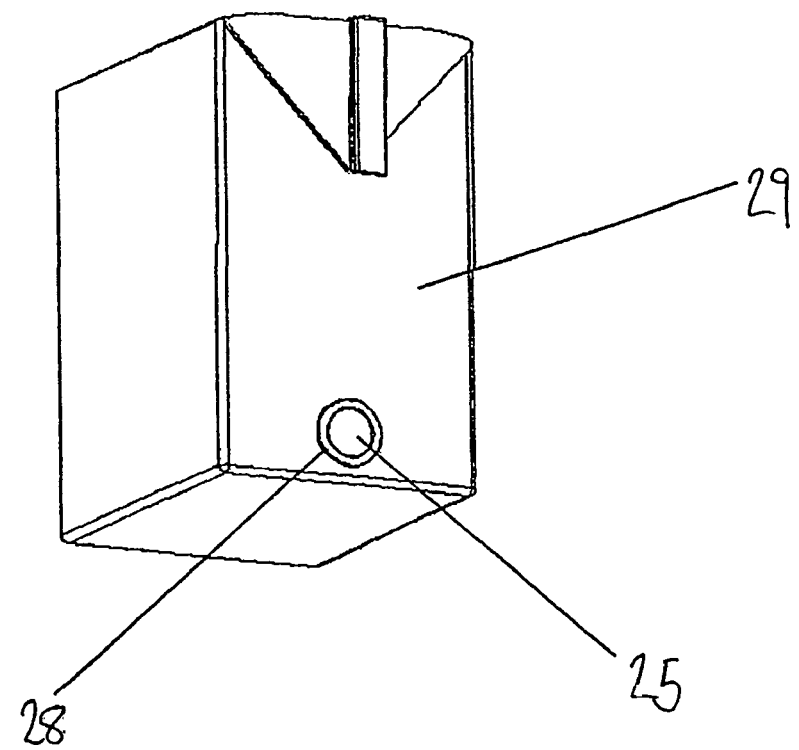
FIG. 18 is a perspective view of the indicator which is shown in FIG. 17 attached to a package for a liquid food.
Figure 19:
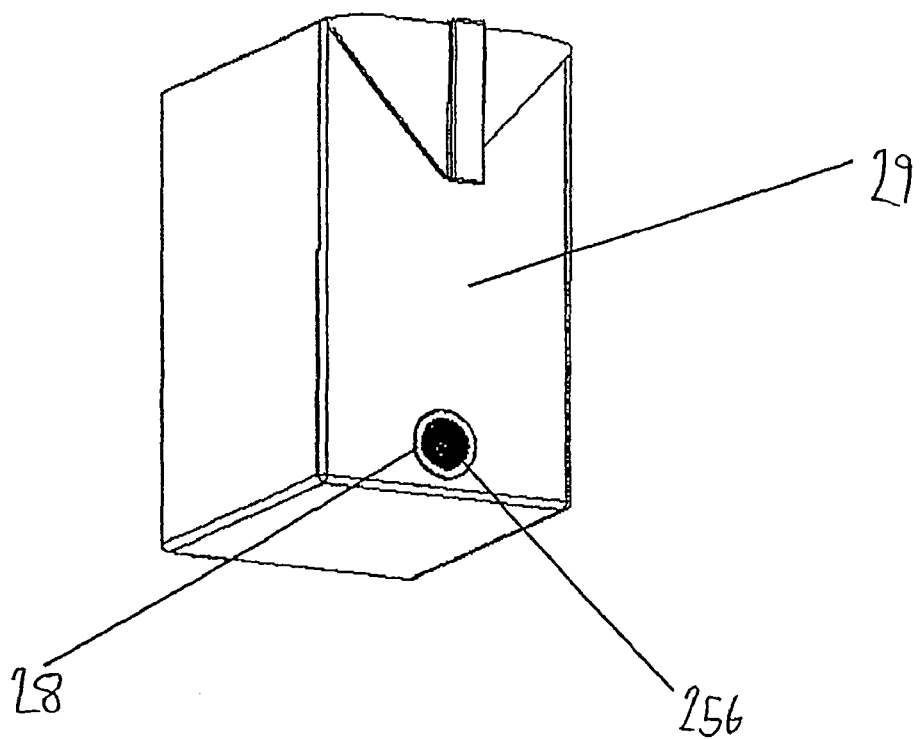
FIG. 19 is a perspective view of the indicator and liquid food package which are shown in FIG. 18 wherein the signalling layer of the indicator is producing a detectable visual signal.

FIGS. 18 and 19 show a food product 29 to which the indicator 25,25b is attached by means of supporting collar 28. In FIG. 19, the signalling layer of indicator 25b is producing a detectable visual signal.

Figure 20:
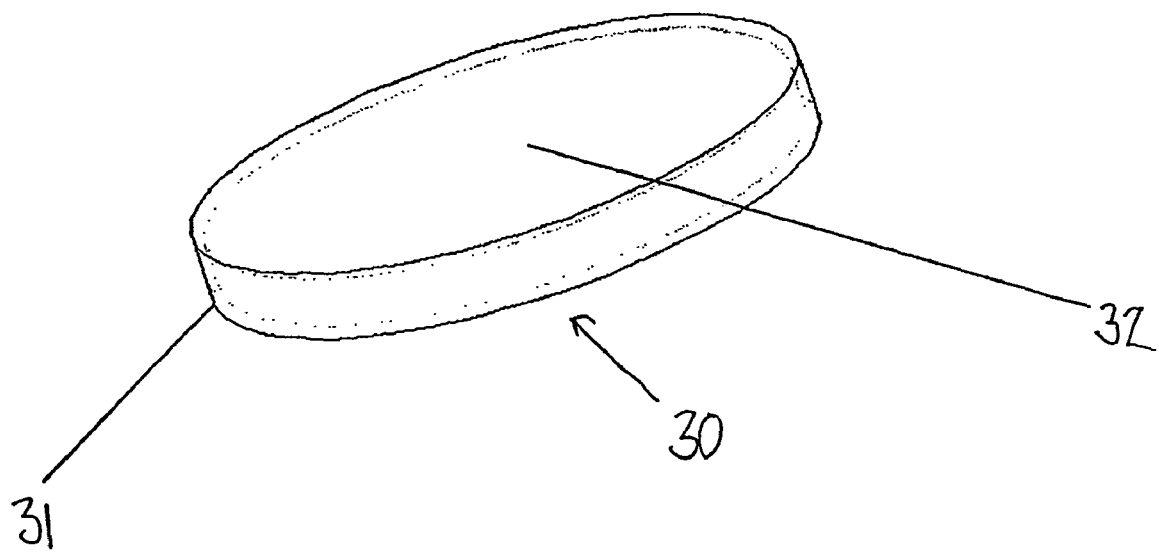
FIG. 20 is a perspective view of a further indicator according to the invention.
Figure 21:
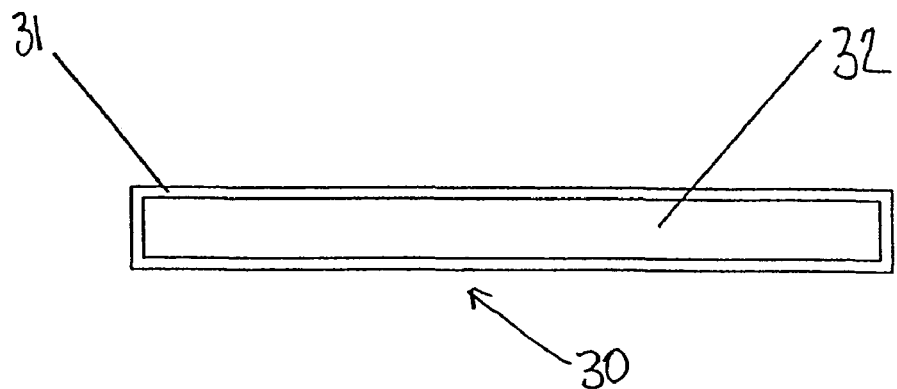
FIG. 21 is a cross-sectional view of the indicator which is shown in FIG. 20.

FIGS. 20 and 21 show a fifth embodiment of the indicator according to the invention. The indicator 30 comprises a biopolymer layer 31 and a signalling layer 32.

Figure 22:
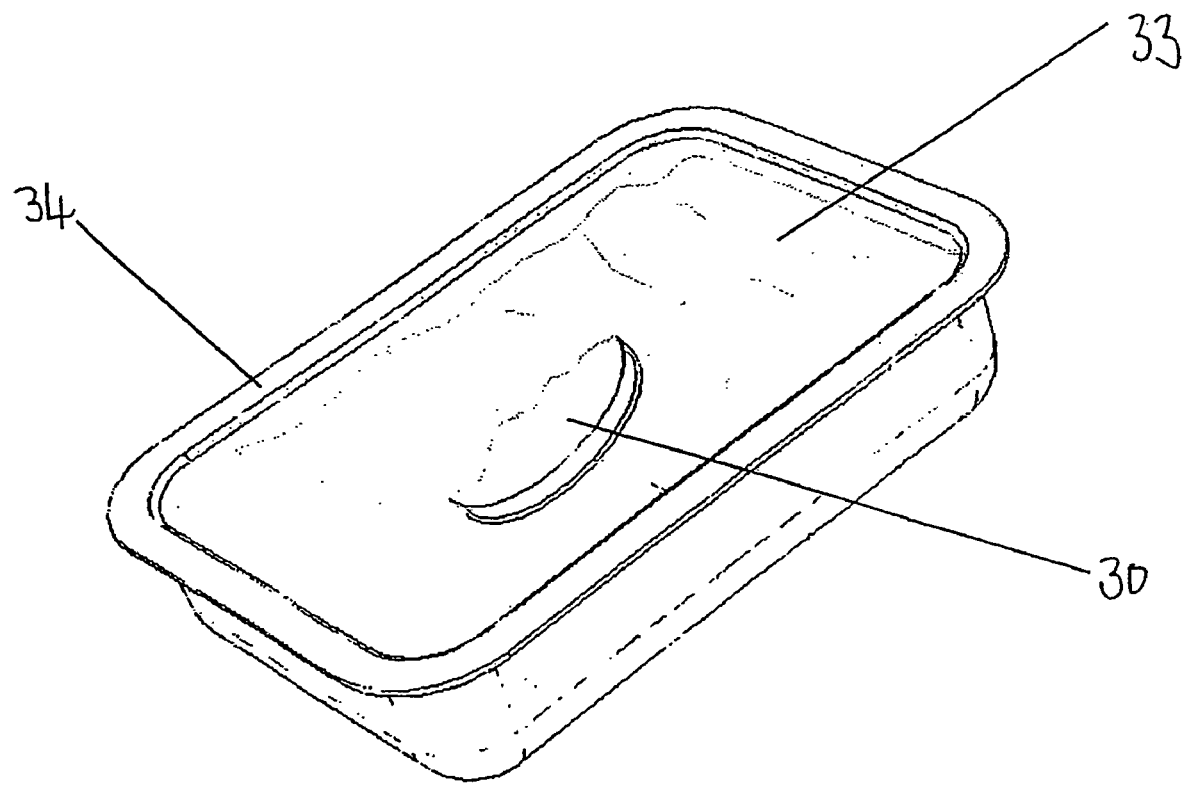
FIG. 22 is a perspective view of a food stuff containing the indicator which is shown in FIGS. 20 and 21.
Figure 23:
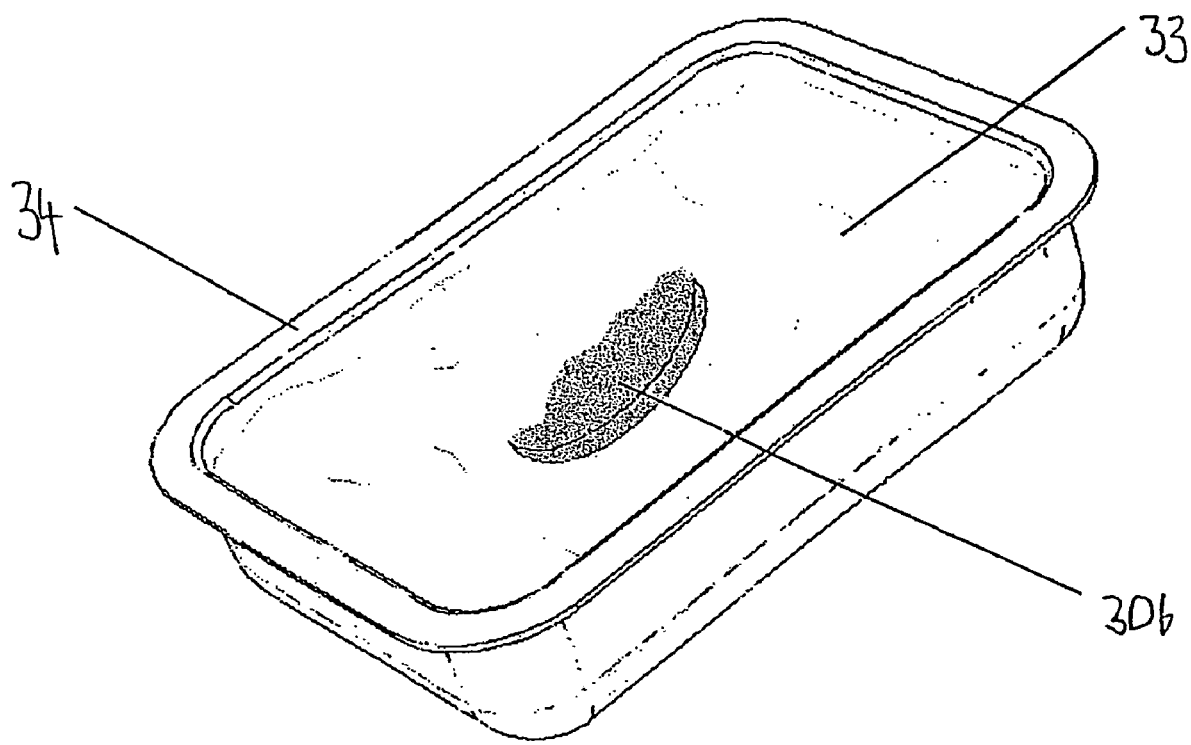
FIG. 23 is a perspective view of the food stuff and indicator which are shown in FIG. 22 wherein the signalling layer of the indicator is producing a detectable signal.

FIGS. 22 and 23 show a foodstuff 33 in a container 34 into which the indicator 30,30b has been inserted. In FIG. 23, the signalling layer of indicator 30b is producing a detectable visual signal.

It is to be understood that the figures are included by way of example only and that the invention covers any variants of the embodiments portrayed.

The present invention is further illustrated by means of the following examples, which are not intended to limit the scope of the present invention.

EXAMPLE 1

Formation of Layer (a)

A chitosan (poly (D-glucosamine) of formula I) membrane

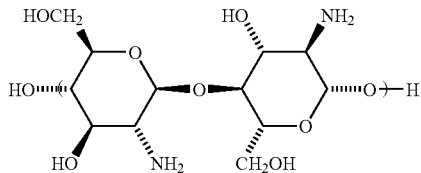

Formula I was formed for use as layer (a) using the method described below:

A homogenous solution of 1% (w/w) purified 60% chitosan was prepared in 1% acetic acid by continuous stirring overnight at 22° C. (room temperature).

20 g of the solution was transferred to a sterile polystyrene petri dish (120×120×17 mm) placed on a level surface at 30° C. for several days until the solution was dry and a uniform membrane was formed.

The resulting membrane was removed carefully and neutralized by immersion for 1 hour in 100 ml 2% (w/v) sodium hydroxide solution.

The film was then washed in distilled water several times over a period of 1 hour.

The swollen film was then placed between glass plates and placed in a drying oven until dry.

The film was then removed from the glass plate.

60% deacetylated chitosan was used as it had been determined experimentally that this level of de-acetylation produced a material having the required mechanical and biochemical characteristics, namely a material which was strong enough to handle and which would degrade in the presence of lysozyme.

EXAMPLE 2

Determination of Concentration of Signalling Substance

Meldola's blue (formula II) and nitro blue tetrazolium (formula III) were chosen for use as indicators.

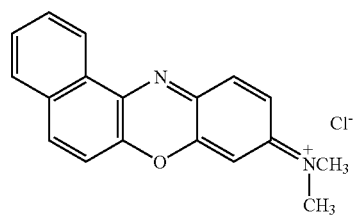

Formula II

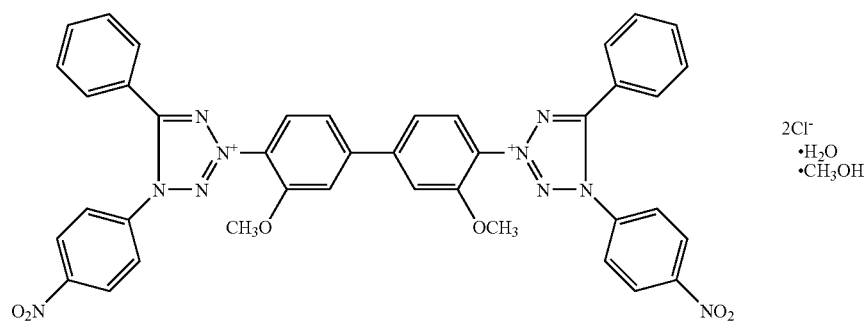

Formula III

Meldola's blue (8-dimethylamino-2,3-benzophenoxazine) acts as an electron donor to tetrazolium salts, such as nitro blue tetrazolium to form an insoluble formazan product. This product is coloured and precipitates out of solution, giving a visual indication of the presence of electron donors such as NADH. The reaction is shown below:

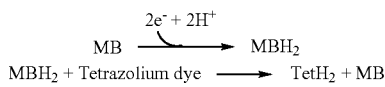

$$MB \xrightarrow{2e^- + 2H^+} MBH_2$$
$$MBH_2 + \text{Tetrazolium dye} \longrightarrow TetH_2 + MB$$

Optimization experiments were carried out to determine the concentrations of meldola's blue and nitro blue tetrazolium in order that the formation of the formazan product (and therefore colour) was increased, and that allowed the meldola's blue to be continuously recycled. NADH was used as the electron donor. The concentrations of meldola's blue (blue crystals) and nitro blue tetrazolium (clear yellow solution) were kept as low as possible so that their presence;
(i) did not colour the reaction mixture at the start of the experiment, but
(ii) was high enough to detect the presence of low concentrations of NADH.

Hence, it was determined that with 10 nmol NADH as the electron donor, the rate of formation of colour was highest with 50 µmol meldola's blue and 0.0025% nitro blue tetrazolium. The rate of reaction was determined to be 0.043 absorbance units (A) per minute.

When the NADH was replaced with foetal calf serum, as expected, there was no colour production, since there was no electron donor present.

*S. aureus* cell suspensions at a concentration of approximately $10^8$ cells/ml in foetal calf serum, with 50 µmol meldola's blue and 0.0025% nitro blue tetrazolium, were able to induce colour production at a rate of approximately 0.04 A/minute.

To mimic wound situations, $10^8$ B cells/ml of *S. aureus* cells grown in foetal calf serum were lysed by several different methods and tested as the electron donor.
(i) Cells lysed by sonication and/or high pressure (French Pressure Cell) to release the cell components, had reaction rates of about 0.06 A/minute.
(ii) Penicillin treatment of cells up to 1 hour, caused the reaction rate to increase to 0.11 A/minute.
(iii) Exposure of the cells to lysozyme for up to 1 hour resulted in a rate equivalent to 0.14 A/minute.

In the absence of meldola's blue the reaction rate was about 0.036 A/minute.

The chemical formulation for this model to effectively measure 10 nmol NADH was therefore determined to be:

| Meldola's blue | 50 µmol |
|---|---|
| NBT | 0.0025% |

EXAMPLE 3

Signalling Presence of Substance

A simple cell with two chambers separated by a vertical wall of chitosan as produced in Example 1 was constructed to demonstrate the degradation of chitosan in a time-dependent manner in the presence of lysozyme. The left hand chamber was filled with a blue coloured dye to which lysozyme was added. The right hand chamber contained water. The chitosan between the two chambers prevented flow of liquid between them.

The diffusion of colour between the chambers was examined for up to 30 minutes. Appropriate controls were run where no lysozyme was present.

Two concentrations of lysozyme (25 and 50 µg per ml) were used, and the strength of colour visible in the second chamber up to 30 minutes was determined. A rough estimation of the relative rate of degradation of the chitosan by lysozyme was therefore given. The results are presented in the table below, the stronger the colour observed, the more positives indicated. Where no lysozyme was present, no diffusion of colour was observed.

| | Lysozyme concentration (mg/ml) | | |
|---|---|---|---|
| Time (mins) | 0 | 25 | 50 |
| 0 | − | − | 0 |
| 10 | − | + | + + |
| 30 | − | + + | + + + + |

It was clearly demonstrated in this model therefore, that two levels of lysozyme could be discriminated in a qualitative way.

The model was then repeated, using meldola's blue and nitro blue tetrazolium to signal the presence of NADH. Experimental work optimised the levels of NADH, NBT and meldola's blue required to give similar discrimination in such a time-course experiment. In this case the left chamber was filled with a solution of NADH and lysozyme, while the right chamber was filled with a solution of meldola's blue and NBT. This set-up was a close approximation to the envisaged final product format, and the results once again demonstrated that the system could discriminate between different levels of lysozyme in a time-dependent manner.

EXAMPLE 4

Method for Production of Indicator

U.S. Pat. No. 5,911,937 (Capitol Specialty Plastics Inc), the content of which is incorporated by reference, details a method which allows for the creation of microscopic interconnecting transmitting channels throughout a solid, water-insoluble polymer. These channels provide pathways that facilitate diffusion of substances through the polymer. Channels are formed by first mixing a polymer, a channelling agent and an active component, heating the mixture above the polymer's melting point and then allowing it to cool. The resultant polymer matrix contains a network of interconnecting channels leading from the surface to the entrapped active particles. The polymer material can be moulded or formed into sheets or fibres. Suitable channelling agents include polyglycol, polyethylene glycol, EVOH, or glycerin. Any thermoplastic material may be used, including, but not limited to, polypropylene, polyethylene, ABS, polystyrene, polycarbonate, Nylon, PVC, thermoplastic elastomers, polyester, and thermosets.

To produce an indicator of the present invention as shown in FIG. 6, the signalling layer is moulded from a mixture of a polymer, a channelling agent and the indicator substances, meldola's blue and nitro blue tetrazolium, to produce a polymer matrix in the form of the disc 7 by the method described above.

The cup shaped biopolymer layer 8, is produced by:

a) Moulding or casting chitosan into the form of a cup of suitable thickness and with suitable internal dimensions as to provide an interference fit with the disc 7. The indicator 6 is assembled by pressing the disc 7 into the cup shaped biopolymer layer 8 in order that one face and the edge of the indicator disc 6 is in contact with, and covered by, the biopolymer layer.

or b) Spray coating chitosan to a suitable thickness onto one face and the edge of the disc 7.

The physical dimensions of the disc 7 and the quantity of the indicator substance entrained within and the thickness and chemical composition of the biopolymer layer 8 are dependent upon the wound management application for which the indicator is intended.

EXAMPLE 5

Second Method for Production of Indicator

To produce an indicator of the present invention as shown in FIG. 6, the indicator substances, meldola's blue and nitro blue tetrazolium are spotted or sprayed or coated onto a nitrocellulose membrane sheet. The nitrocellulose retains the indicator molecules by electrostatic charge thereby preventing the leaching of reagents from the indicator through the biopolymer layer and into, for example, a wound. The signalling layer of the indicator 6 is then cut from the nitrocellulose membrane sheet to form the disc 7.

The cup shaped biopolymer layer 8, is produced by:

a) Moulding or casting chitosan into the form of a cup of suitable thickness and with suitable internal dimensions as to provide an interference fit with the disc 7. The indicator 6 is assembled by pressing the disc 7 into the cup shaped biopolymer layer 8 in order that one face and the edge of the indicator disc 6 is in contact with, and covered by, the biopolymer layer.

or b) Spray coating chitosan to a suitable thickness onto one face and the edge of the disc 7.

The physical dimensions of the disc 7, the quantity of the indicator substances bound to the nitrocellulose membrane and the thickness and chemical composition of the biopolymer layer 8 are dependent upon the wound management application for which the indicator is intended.

EXAMPLE 6

Third Method for Production of Indicator

To produce an indicator of the present invention as shown in FIG. 12, the signalling layer is formed from a mixture of a polymer, a channelling agent and the indicator substances, meldola's blue and nitro blue tetrazolium, using the method described in Example 4 to produce a polymer matrix in the form of a thread 16.

The biopolymer layer 17 is produced by:

a) Spray coating chitosan to a suitable thickness onto the surface of the thread 16 or b) Dipping the thread 16 into a bath of chitosan to produce a coating of suitable thickness.

The thickness of the thread 16 and the quantity of the indicator substance entrained within and the thickness and chemical composition of the biopolymer layer 17 are dependent upon the wound management application for which the indicator is intended.

The invention claimed is:

1. An indicator suitable for detecting at a location the presence of lysozyme or the presence of nicotinamide adenine dinucleotide (NADH) in the presence of lysozyme, wherein the indicator comprises:
   (a) a biopolymer layer which is susceptible to degradation by lysozyme; and
   (b) a signaling layer which comprises an indicator substance, which layer is adapted to produce a detectable signal upon contact with lysozyme or upon contact with NADH in the presence of lysozyme;
   wherein, in use, the signaling layer (b) is at least initially protected from contact with NADH by the layer (a), and wherein
   the signaling layer (b) is adapted to produce a detectable signal whose initial strength is proportional to the amount of NADH or lysozyme, and wherein the signaling layer (b) further comprises a pH indicator or assay reagents for detecting an additional enzyme, an immune cell or a micro-organism.

2. The indicator according to claim 1 wherein the detectable signal is a visually detectable signal.

3. The indicator according to claim 1 wherein the signalling layer (b) further comprises a moisture sensitive indicator.

4. The indicator according to claim 3 wherein the moisture sensitive indicator is silica or cobalt chloride.

5. The indicator according to claim 1 wherein layer (a) wholly encapsulates layer (b).

6. The indicator according to claim 1 which is provided with a protective layer.

7. The indicator according to claim 6 wherein the protective layer is substantially transparent to the detectable signal produced by the signalling layer.

8. An indicator suitable for detecting at a location the presence of lysozyme or the presence of nicotinamide adenine dinucleotide (NADH) in the presence of lysozyme, wherein the indicator comprises:
   (a) a biopolymer layer which is susceptible to degradation by lysozyme; and
   (b) a signaling layer which comprises an indicator substance, which layer is adapted to produce a detectable signal upon contact with lysozyme or upon contact with NADH in the presence of lysozyme;
   wherein, in use, the signaling layer (b) is at least initially protected from contact with NADH by the layer (a), and wherein the location is a human, animal, domestic, laboratory or industrial location,
     foodstuff or personal care product, and wherein the signaling layer (b) further comprises a pH indicator or assay reagents for
     detecting an additional enzyme, an immune cell or a micro-organism.

9. An indicator suitable for detecting at a location the presence of lysozyme or the presence of nicotinamide adenine dinucleotide (NADH) in the presence of lysozyme, wherein the indicator comprises:
   (a) a biopolymer layer which is susceptible to degradation by lysozyme; and (b) a signalling layer which comprises an indicator substance, which layer is adapted to produce a detectable signal upon contact with lysozyme or upon contact with NADH in the presence of lysozyme;

wherein, in use, the signalling layer (b) is at least initially protected from contact with NADH by the layer (a), and wherein the signalling layer (b) is adapted to produce a detectable signal whose initial strength is proportional to the amount of NADH or lysozyme, and wherein the signalling layer (b) comprises methylene blue, meldola's blue, phenol red, bromo-chloro-indolyl phosphate, alanine amidoacridone, fluorescein diacetate and/or a tetrazolium salt.

10. The indicator according to claim 9 wherein the signalling layer (b) comprises meldola's blue and nitro blue tetrazolium.

11. An indicator according to claim 1 which suitable for detecting at a location the presence of lysozyme or the presence of nicotinamide adenine dinucleotide (NADH) in the presence of lysozyme, wherein the indicator comprises:

(a) a biopolymer layer which is susceptible to degradation by lysozyme; and (b) a signaling layer which comprises an indicator substance, which layer is adapted to produce a detectable signal upon contact with lysozyme or upon contact with NADH in the presence of lysozyme;

wherein, in use, the signaling layer (b) is at least initially protected from contact with NADH by the layer (a), and wherein the signaling layer (b) is adapted to produce a detectable signal whose initial strength is proportional to the amount of NADH or lysozyme, wherein the signaling layer (b) further comprises a pH indicator or assay reagents for detecting an additional enzyme, an immune cell or a micro-organism and wherein the indicator is in the form of a disc or a tube.

12. An indicator suitable for detecting at a location the presence of lysozyme or the presence of nicotinamide adenine dinucleotide (NADH) in the presence of lysozyme, wherein the indicator comprises:

(a) a biopolymer layer which is susceptible to degradation by lysozyme; and (b) a signaling layer which comprises an indicator substance, which layer is adapted to produce a detectable signal upon contact with lysozyme or upon contact with NADH in the presence of lysozyme;

wherein, in use, the signaling layer (b) is at least initially protected from contact with NADH by the layer (a), and wherein the signaling layer (b) is adapted to produce a detectable signal whose initial strength is proportional to the amount of NADH or lysozyme, wherein the signalling layer (b) further comprises a DH indicator or assay reagents for detecting an additional enzyme, an immune cell or a micro-organism and wherein the indicator is for use in a liquid environment and is protected from contact with the environment at least initially.

13. An indicator suitable for detecting at a location the presence of lysozyme or the presence of nicotinamide adenine dinucleotide (NADH) in the presence of lysozyme, wherein the indicator comprises:

(a) a biopolymer layer which is susceptible to degradation by lysozyme; and (b) a signaling layer which comprises an indicator substance, which layer is adapted to produce a detectable signal upon contact with lysozyme or upon contact with NADH in the presence of lysozyme; wherein, in use, the signaling layer (b) is at least initially protected from contact with NADH by the layer (a), and wherein the signaling layer (b) is adapted to produce a detectable signal whose initial strength is proportional to the amount of NADH or lysozyme, wherein the signalling layer (b) further comprises a pH indicator or assay reagents for detecting an additional enzyme, an immune cell or a micro-organism and wherein the indicator is for use in an aqueous environment and is protected from contact with the environment at least initially.

14. An indicator suitable for detecting at a location the presence of lysozyme or the presence of nicotinamide adenine dinucleotide (NADH) in the presence of lysozyme, wherein the indicator comprises:

(a) a biopolymer layer which is susceptible to degradation by lysozyme; and (b) a signaling layer which comprises an indicator substance, which layer is adapted to produce a detectable signal upon contact with lysozyme or upon contact with NADH in the presence of lysozyme;

wherein, in use, the signaling layer (b) is at least initially protected from contact with NADH by the layer (a), and wherein the signaling layer (b) is adapted to produce a detectable signal whose initial strength is proportional to the amount of NADH or lysozyme, wherein the signalling layer (b) further comprises a pH indicator or assay reagents for detecting an additional enzyme, an immune cell or a micro-organism and wherein the indicator is for use in a tissue culture medium or a foodstuff and is protected from contact with the tissue culture medium or foodstuff at least initially.

15. A dressing for a wound which comprises a dressing layer and an indicator suitable for detecting at a location the presence of lysozyme or the presence of nicotinamide adenine dinucleotide (NADH) in the presence of lysozyme, wherein the indicator comprises:

(a) a biopolymer layer which is susceptible to degradation by lysozyme; and (b) a signalling layer which comprises an indicator substance, which layer is adapted to produce a detectable signal upon contact with lysozyme or upon contact with NADH in the presence of lysozyme;

wherein, in use, the signalling layer (b) is at least initially protected from contact with NADH by the layer (a), and wherein the signalling layer (b) is adapted to produce a detectable signal whose initial strength is proportional to the amount of NADH or lysozyme.

16. A dressing according to claim 15 which includes an additional layer which is an adhesive layer and/or a removable protective layer.

17. A dressing according to claim 15 which additionally comprises a moisture indicator.

18. A dressing according to claim 15 wherein, in use, the signalling layer is visible.

19. A suture which comprises an indicator suitable for detecting at a location the presence of lysozyme or the presence of nicotinamide adenine dinucleotide (NADH) in the presence of lysozyme, wherein the indicator comprises:

(a) a biopolymer layer which is susceptible to degradation by lysozyme; and (b) a signalling layer which comprises an indicator substance, which layer is adapted to produce a detectable signal upon contact with lysozyme or upon contact with NADH in the presence of lysozyme;

wherein, in use, the signalling layer (b) is at least initially protected from contact with NADH by the layer (a), and wherein the signalling layer (b) is adapted to produce a detectable signal whose initial strength is proportional to the amount of NADH or lysozyme.

20. Packaging for a foodstuff which packaging comprises a container layer and an indicator suitable for detecting at a location the presence of lysozyme or the presence of nicotinamide adenine dinucleotide (NADH) in the presence of lysozyme, wherein the indicator comprises:

(a) a biopolymer layer which is susceptible to degradation by lysozyme; and (b) a signalling layer which comprises an indicator substance, which layer is adapted to produce a detectable signal upon contact with lysozyme or upon contact with NADH in the presence of lysozyme;

wherein, in use, the signalling layer (b) is at least initially protected from contact with NADH by the layer (a), and wherein the signalling layer (b) is adapted to produce a detectable signal whose initial strength is proportional to the amount of NADH or lysozyme.

21. Packaging according to claim 20 wherein, in use, the layer (a) of the indicator is in contact with the foodstuff.

22. Packaging according to claim 20 wherein, in use, the signalling layer is visible.

23. Packaging according to claim 20 wherein the indicator is incorporated into the container layer.

24. A process for the production of an indicator suitable for detecting at a location the presence of lysozyme or the presence of nicotinamide adenine dinucleotide (NADH) in the presence of lysozyme, wherein the indicator comprises:

(a) a biopolymer layer which is susceptible to degradation by lysozyme; and (b) a signaling layer which comprises an indicator substance, which layer is adapted to produce a detectable signal upon contact with lysozyme or upon contact with NADH in the presence of lysozyme; wherein, in use, the signaling layer (b) is at least initially protected from contact with NADH by the layer (a), and wherein the signaling layer (b) is adapted to produce a detectable signal whose initial strength is proportional to the amount of NADH or lysozyme and wherein the signalling layer (b) further comprises a chromogenic or fluorogenic substrate, which process comprises: forming the signaling layer (b) from a thermoplastic material, a channeling agent and the indicator substance, forming the degradable biopolymer layer (a), and then assembling the layer (a) onto the layer (b).

25. The process according to claim 24 wherein the signalling layer is formed by coating, spotting or spraying indicator onto a membrane.

26. The process according to claim 24 wherein the degradable biopolymer layer is formed by moulding or casting said biopolymer.

27. The process according to claim 24 wherein the degradable biopolymer layer is formed by spray coating said biopolymer onto the signalling layer.

28. The process according to claim 24 wherein the degradable biopolymer layer is formed by dipping the signalling layer into a bath of said biopolymer.

* * * * *